United States Patent [19]

Spencer

[11] Patent Number: 5,382,525
[45] Date of Patent: Jan. 17, 1995

[54] METHOD OF EFFECTING INCREASED PERFORMANCE OF DIAGNOSTIC ENZYME REACTION SYSTEMS USING NOBLE GASES

[75] Inventor: Kevin C. Spencer, Hinsdale, Ill.

[73] Assignee: American Air Liquide, Walnut Creek, Calif.

[21] Appl. No.: 982,493

[22] Filed: Nov. 27, 1992

[51] Int. Cl.$^6$ .................... C12N 1/38; C12Q 1/00; A61K 33/00
[52] U.S. Cl. ........................... 435/244; 435/4; 424/600
[58] Field of Search ............... 435/4, 244; 424/600

[56] References Cited

U.S. PATENT DOCUMENTS

| | | | |
|---|---|---|---|
| 2,569,217 | 9/1951 | Bagdigian | 99/68 |
| 3,143,471 | 8/1964 | Coady | 167/78 |
| 3,183,171 | 5/1965 | Schreiner | 435/244 |
| 3,378,443 | 4/1968 | Cooper et al. | 167/78 |
| 3,677,024 | 7/1972 | Segall | 62/64 |
| 3,725,076 | 4/1973 | Stefanucci et al. | 99/68 |
| 3,957,892 | 5/1976 | Kleiman | 260/652.5 R |
| 4,008,754 | 2/1977 | Kraushaar et al. | 165/2 |
| 4,017,363 | 4/1977 | McMullen et al. | 195/31 R |
| 4,044,004 | 8/1977 | Saucy et al. | 260/239.55 C |
| 4,136,049 | 1/1979 | Horiishi et al. | 252/62.56 |
| 4,138,565 | 2/1979 | Ehrhardt et al. | 544/346 |
| 4,308,264 | 12/1981 | Conway et al. | 424/236 |
| 4,314,810 | 2/1982 | Fourcadier et al. | 8/410 |
| 4,315,266 | 2/1982 | Ellis, Jr. | 343/895 |
| 4,450,960 | 5/1984 | Johnson | 206/334 |
| 4,496,397 | 1/1985 | Waite | 106/161 |
| 4,501,814 | 2/1985 | Schoenrock et al. | 435/94 |
| 4,548,605 | 10/1985 | Iwamoto et al. | 604/410 |
| 4,622,425 | 11/1986 | Gagne | 562/595 |
| 4,664,256 | 5/1987 | Halskov | 206/213.1 |
| 4,812,320 | 3/1989 | Ruzek | 426/393 |
| 4,830,858 | 3/1989 | Payne et al. | 424/450 |
| 4,892,579 | 1/1990 | Hazelton | 75/0.5 B |
| 4,895,726 | 1/1990 | Curtet et al. | 424/456 |
| 4,895,729 | 1/1990 | Powrie et al. | 426/316 |
| 4,919,955 | 4/1990 | Mitchell | 426/394 |
| 4,946,326 | 8/1990 | Schvester et al. | 426/316 |
| 4,965,165 | 10/1990 | Saccocio et al. | 430/138 |
| 4,971,813 | 11/1990 | Strobel et al. | 426/51 |
| 5,004,623 | 4/1991 | Giddey et al. | 426/564 |
| 5,006,222 | 4/1991 | Sequeria, Jr. | 208/33 |
| 5,021,251 | 6/1991 | McKenna et al. | 426/330.5 |
| 5,030,778 | 7/1991 | Ransford | 570/208 |
| 5,045,529 | 9/1991 | Chiang | 514/6 |
| 5,064,070 | 11/1991 | Higashiyama | 206/455 |
| 5,108,656 | 4/1992 | Schvester et al. | 252/380 |
| 5,128,160 | 7/1992 | Fath et al. | 426/316 |

FOREIGN PATENT DOCUMENTS

| | | |
|---|---|---|
| 989311 | 5/1976 | Canada. |
| 0111595 | 6/1984 | European Pat. Off.. |
| 0346201 | 12/1989 | European Pat. Off.. |
| 0412155 | 2/1991 | European Pat. Off.. |
| 0440273 | 8/1991 | European Pat. Off.. |
| 1339669 | 9/1963 | France. |
| 1454653 | 8/1966 | France. |
| 2261518 | 9/1975 | France. |
| 2406567 | 5/1979 | France. |
| 2643232 | 8/1990 | France. |
| 3007712 | 10/1981 | Germany. |
| 52-27699 | 9/1972 | Japan. |
| 52-86987 | 7/1977 | Japan. |
| 52-97913 | 8/1977 | Japan. |

(List continued on next page.)

OTHER PUBLICATIONS

Federation Proceedings, vol. 26, No. 2, Mar.–Apr. 1967, pp. 650, G. F. Doebbler, et al., "Inert Gas Interactions and Effects on Enzymatically Active Proteins".

(List continued on next page.)

Primary Examiner—Michael G. Wityshyn
Assistant Examiner—Ralph Gitomer
Attorney, Agent, or Firm—Oblon, Spivak, McClelland, Maier & Neustadt

[57] ABSTRACT

A method of effecting increased performance of diagnostic enzyme reaction systems which includes contacting at least one reagent of an enzyme-diagnostic kit during use of the reagent in conjuction with the kit with a noble gas, mixture of noble gases or gas mixtures containing at least one noble gas.

21 Claims, No Drawings

FOREIGN PATENT DOCUMENTS

| | | |
|---|---|---|
| 54-129185 | 10/1979 | Japan . |
| 1-059647 | 1/1980 | Japan . |
| 58-39650 | 3/1983 | Japan . |
| 60-56984 | 4/1985 | Japan . |
| 63-77848 | 4/1988 | Japan . |
| 2-104502 | 4/1990 | Japan . |
| 3-200568 | 9/1991 | Japan . |
| 0415656 | 8/1934 | United Kingdom . |
| 1376362 | 12/1974 | United Kingdom . |
| 2029846 | 3/1980 | United Kingdom . |
| 2091556 | 8/1982 | United Kingdom . |
| 1289437 | 2/1987 | U.S.S.R. . |

OTHER PUBLICATIONS

Febs Letters, vol. 62, No. 3, Mar. 1976, pp. 284–287, K. Sandhoff, et al., "Effect of Xenon, Nitrous Oxide and Halothane on Membrane-Bound Sialidase from Calf Brain".

Aviation, Space and Environmental Medicine, vol. 48, No. 1, Jan. 1977, pp. 40–43, S. K. Hemrick, et al., "Effect of Increased Pressures of Oxygen, Nitrogen, and Helium on Activity of a Na–K–Mg AtPase of Beef Brain".

Chemical Abstracts, vol. 80, No. 7, AN–35579z 1973.
Chemical Abstracts, vol. 80, No. 11, AN–56112g.
Chemical Abstracts, vol. 86, No. 3, AN–14672h.
Chemical Abstracts, vol. 87, No. 22, AN–172800y.
Chemical Abstracts, vol. 91, No. 17, AN–138183x.
Chemical Abstracts, vol. 93, No. 24, AN–225670p.

Undersea Biomedical Research, vol. 17, No. 4, 1990, pp. 297–303, J. S. Colton, et al., "Effect of Helium and Heliox on Glutamate Decarboxylase Activity".

Sciences Des Aliments, vol. 4, No. 4, 1984, pp. 595–608, B. Pichard, et al., "Effect of Nitrogen, Carbon Monoxide and Carbon Dioxide on the Activity of Proteases of Pseudomonas Fragi and Streptomyces Caespitosus".

Chemical Abstracts, vol. 97, No. 18, AN–145890c.
Chemical Abstracts, vol. 98, No. 10, AN–78191f.
Chemical Abstracts, vol. 99, No. 21, AN–172397v.
Chemical Abstracts, vol. 106, No. 25, AN–210601e.
Chemical Abstracts, vol. 115, No. 20, AN–214644e.
WPI Abstracts, AN–70–84762R, DE–1753586.
WPI Abstracts, AN–82–05785E, DE–3 202 622, Sep. 9, 1982.

Federation Proceedings, vol. 27, No. 3, May–Jun. 1968, H. R. Schreiner, "General Biological Effects of the Helium–Xenon Series of Elements".

156 Food Technology, vol. 34, No. 6, Jun. 1980, p. 102.

Sandhoff R., Effect of Xenon, $N_2O$ & Halothang on . . . Febs Letters 62 #3 1976, pp. 284–287.

Doebbler G. F., Inert Gas Interactions & Effects on . . . Federation Proceedings vol. 26 1967 p. 650.

Schreiner H. R., General Biological Effects of the . . . Federation Proceedings vol. 27 1968 pp. 872–878.

METHOD OF EFFECTING INCREASED PERFORMANCE OF DIAGNOSTIC ENZYME REACTION SYSTEMS USING NOBLE GASES

BACKGROUND OF THE INVENTION

1. Field of the Invention

The present invention relates to a method of effecting improved performance of diagnostic enzyme reaction systems using noble gases.

2. Description of the Background

The ability of the noble gases helium (He), neon (Ne), argon (Ar), krypton (Kr), xenon (Xe) and radon (Ra) to enter into chemical combination with other atoms is extremely limited. Generally, only krypton, xenon and radon have been induced to react with other atoms which are highly reactive, such as fluorine and oxygen, and the compounds thus formed are explosively unstable. See *Advanced Inorganic Chemistry*, by F. A. Cotton and G. Wilkinson (Wiley, Third Edition). However, while the noble gases are, in general, chemically inert, xenon is known to exhibit certain physiological effects, such as anesthesia. Other physiological effects have also been observed with other inert gases such as nitrogen, which, for example, is known to cause narcosis when used under great pressure in deep-sea diving.

It has been reported in U.S. Pat. No. 3,183,171 to Schreiner that argon and other inert gases can influence the growth rate of fungi and argon is known to improve the preservation of fish or seafood. U.S. Pat. No. 4,946,326 to Schvester, JP 52105232, JP 80002271 and JP 77027699. However, the fundamental lack of understanding of these observations clearly renders such results difficult, if not impossible, to interpret. Moreover, the meaning of such observations is further obscured by the fact that mixtures of many gases, including oxygen, were used in these studies. Further, some of these studies were conducted at hyperbaric pressures and at freezing temperatures. At such high pressures, it is likely that the observed results were caused by pressure damage to cellular components and to the enzymes themselves.

For example, from 1964 to 1966, Schreiner documented the physiological effects of inert gases particularly as related to anesthetic effects and in studies relating to the development of suitable containment atmospheres for deep-sea diving, submarines and spacecraft. The results of this study are summarized in three reports, each entitled: "Technical Report. The Physiological Effects of Argon, Helium and the Rare Gases," prepared for the Office of Naval Research, Department of the Navy. Contract Nonr 4115(00), NR: 102-597. Three later summaries and abstracts of this study were published.

One abstract, "Inert Gas Interactions and Effects on Enzymatically Active Proteins," *Fed. Proc.* 26:650 (1967), restates the observation that the noble and other inert gases produce physiological effects at elevated partial pressures in intact animals (narcosis) and in microbial and mammalian cell systems (growth inhibition).

A second abstract, "A Possible Molecular Mechanism for the Biological Activity of Chemically Inert Gases," In: Intern. Congr. Physiol. Sci., 23rd, Tokyo, restates the observation that the inert gases exhibit biological activity at various levels of cellular organization at high pressures.

Also, a summary of the general biological effects of the noble gases was published by Schreiner in which the principal results of his earlier research are restated. "General Biological Effects of the Helium-Xenon Series of Elements," *Fed. Proc.* 27:872-878 (1968).

However, in 1969, Behnke et al refuted the major conclusions of Schreiner. Behnke et al concluded that the effects reported earlier by Schreiner are irreproducible and result solely from hydrostatic pressure, i.e., that no effects of noble gases upon enzymes are demonstrable. "Enzyme-Catalyzed Reactions as Influenced by Inert Gases at High Pressures." *J. Food Sci.* 34:370-375.

In essence, the studies of Schreiner were based upon the hypothesis that chemically inert gases compete with oxygen molecules for cellular sites and that oxygen displacement depends upon the ratio of oxygen to inert gas concentrations. This hypothesis was never demonstrated as the greatest observed effects (only inhibitory effects were observed) were observed with nitrous oxide and found to be independent of oxygen partial pressure. Moreover, the inhibition observed was only 1.9% inhibition per atmosphere of added nitrous oxide.

In order to refute the earlier work of Schreiner, Behnke et al independently tested the effect of high hydrostatic pressures upon enzymes, and attempted to reproduce the results obtained by Schreiner. Behnke et al found that increasing gas pressure of nitrogen or argon beyond that necessary to observe a slight inhibition of chymotrypsin, invertase and tyrosinase caused no further increase in inhibition, in direct contrast to the finding of Schreiner.

The findings of Behnke et al can be explained by simple initial hydrostatic inhibition, which is released upon stabilization of pressure. Clearly, the findings cannot be explained by the chemical-$O_2$/inert gas interdependence as proposed by Schreiner. Behnke et al concluded that high pressure inert gases inhibit tyrosinase in non-fluid (i.e., gelatin) systems by decreasing oxygen availability, rather than by physically altering the enzyme. This conclusion is in direct contrast to the findings of Schreiner.

In addition to the refutation by Behnke et al, the results reported by Schreiner are difficult, if not impossible, to interpret for other reasons as well.

First, all analyses were performed at very high pressure, and were not controlled for hydrostatic pressure effects.

Second, in many instances, no significant differences were observed between the various noble gases, nor between the noble gases and nitrogen.

Third, knowledge of enzyme mode of action and inhibition was very poor at the time of these studies, as were the purities of enzymes used. It is impossible to be certain that confounding enzyme activities were not present or that measurements were made with a degree of resolution sufficient to rank different gases as to effectiveness. Further, any specific mode of action could only be set forth as an untestable hypothesis.

Fourth, solubility differences between the various gases were not controlled, nor considered in the result.

Fifth, all tests were conducted using high pressures of inert gases superimposed upon 1 atmosphere of air, thus providing inadequate control of oxygen tension.

Sixth, all gas effects reported are only inhibitions.

Seventh, not all of the procedures in the work have been fully described, and may not have been experimentally controlled. Further, long delays after initiation of the enzyme reaction precluded following the entire course of reaction, with resultant loss of the highest readable rates of change.

Eighth, the reported data ranges have high variability based upon a small number of observations, thus precluding significance.

Ninth, the levels of inhibition observed are very small even at high pressures.

Tenth, studies reporting a dependence upon enzyme concentration do not report significant usable figures.

Eleventh, all reports of inhibitory potential of inert gases at low pressures, i.e., <2 atm., are postulated based upon extrapolated lines from high pressure measurements, not actual data.

Finally, it is worthy of reiterating that the results of Behnke et al clearly contradict those reported by Schreiner in several crucial respects, mainly that high pressure effects are small and that hydrostatic effects, which were not controlled by Schreiner, are the primary cause of the incorrect conclusions made in those studies.

Additionally, although it was reported by Sandhoff et al, FEBS Letters, vol. 62, no. 3 (March, 1976) that xenon, nitrous oxide and halothane enhance the activity of particulate sialidase, these results are questionable due to the highly impure enzymes used in this study and are probably due to inhibitory oxidases in the particles.

To summarize the above patents and publications and to mention others related thereto, the following is noted.

Behnke et al (1969), disclose that enzyme-catalyzed reactions are influenced by inert gases at high pressures. *J. Food Sci.* 34: 370–375.

Schreiner et al (1967), describe inert gas interactions and effects on enzymatically, active proteins. Abstract No. 2209. *Fed. Proc.* 26:650.

Schreiner, H. R. 1964, Technical Report, describes the physiological effects of argon, helium and the rare gases. Contract Nonr 4115 (00), NR: 102-597. Office of Naval Research, Washington, D.C.

Schreiner, H. R. 1965, Technical Report, describes the physiological effects of argon, helium and the rare gases. Contract Nonr 4115 (00), NR: 102-597. Office of Naval Research, Washington, D.C.

Schreiner, H. R. 1966, Technical Report, describes the physiological effects of argon, helium and the rare gases. Contract Nonr 4115 (00), NR: 102-597. Office of Naval Research, Washington, D.C.

Doebbler, G. F. et al, *Fed. Proc.* Vol. 26, p. 650 (1967) describes the effect of pressure or of reduced oxygen tension upon several different enzymes using the gases Kr, Xe, $SF_6$, $N_2O$, He, Ne, Ar and $N_2$. All gases were considered equal in their effect.

Colten et al, *Undersea Biomed. Res.* 17(4), 297–304 (1990) describes the combined effect of helium and oxygen with high pressure upon the enzyme glutamate decarboxylase. Notably, only the hyperbaric inhibitory effect of both helium and oxygen and the chemical inhibitory effect of oxygen was noted.

Nevertheless, at present, it is known that enzyme activities can be inhibited in several ways. For example, many enzymes can be inhibited by specific poisons that may be structurally related to their normal substrates. Alternatively, many different reagents are known to be specific inactivators of target enzymes. These reagents generally cause chemical modification at the active site of the enzyme to induce loss of catalytic activity, active-site-directed irreversible inactivation or affinity labeling. See *Enzymatic Reaction Mechanisms* by C. Walsh (W. H. Freeman & Co., 1979). Alternatively, certain multi-enzyme sequences are known to be regulated by particular enzymes known as regulatory or allosteric enzymes. See *Bioenergetics*, by A. L. Leninger (Benjamin/Cummings Publishing Co., 1973).

Enzymes are commercially used as active constituents of medical and other diagnostic machine systems or procedures. Many applications of these enzyme-based diagnostic machine packages, or procedures are found in the clinical field, for diagnosing diseases, or determining the nature or concentration of certain metabolic compounds or drugs in patients.

Enzyme-based diagnostic procedures involving in vitro testing, which are usually automated, the use of which consists of determining the concentration of a particular substrate compound usually must afford accurate results by using an enzyme which is highly specific for the compound.

When the enzyme specific for the compound of interest does not generate a product that can be monitored easily, such as by ultraviolet/visible spectrophotometry or fluorescence, the first enzymatic reaction can be coupled to a second enzymatic reaction, whose reaction product can be easily measured.

In certain instances, a compound concentration can be determined from the rate of reaction instead of its equilibrium. This is often the case for a compounds that are not substrates, but inhibitors, activators or prosthetic groups. Such compounds may be antibiotics or heavy metals, for example.

It would be generally advantageous for all of the above systems if a means could be provided by which the response time of enzymatic reactions could be accelerated without comprising the accuracy of the results. This would increase the results obtained per unit time, and, hence, the productivity of the system. This would occur if the rate or yield of enzymes used in diagnostics could be increased or otherwise concentrated.

SUMMARY OF THE INVENTION

Accordingly, it is an object of the present invention to provide a method for effecting improved performance of diagnostic enzyme reaction systems.

It is, moreover, an object of the present invention to accomplish the above using noble gases.

The above objects and others,. which will become apparent in view of the following, are provided by a method for effecting improved performance of diagnostic enzyme reaction systems, which entails contacting at least one reagent of an enzyme-based diagnostic system during use of the reagent in conjunction with the system with a noble gas, mixture of noble gases or gas mixture containing at least one noble gas.

DETAILED DESCRIPTION OF THE PREFERRED EMBODIMENTS

In accordance with the present invention, it has been surprisingly discovered that by packaging at least one reagent of an enzyme-based diagnostic system or by conducting the diagnostic enzymatic reaction in the presence of a noble gas, mixture of noble gases or gas mixture containing at least one noble gas, the response time of the reaction may be shortened, thereby allowing a gain in productivity as measured by the number of analyses performed per unit of time.

Furthermore, it has been found that when the present invention is used in conjunction with an automated analyzer, the throughput of the automated analyzer may be increased by placing the reacting chamber of the apparatus under the gas or gases of the present invention. The present invention may be used, however, regardless of whether or not the enzyme is immobilized.

Generally, in accordance with the present invention, one or more reagents of enzyme-based diagnostic systems may be packed under a noble gas, mixture of noble gases or gas mixture containing at last one noble gas, in order to reduce the response time of the enzyme or enzymes used in conjunction with the kit. This affords a gain in productivity as measured by the increased number of analyses performed per unit of time. Alternatively, noble gas may be introduced into the automated diagnostic machine so as to control the enzyme and increase productivity.

The present invention may be used in conjunction with any type of enzyme-based diagnostic reaction or system. The following may be noted as non-limitative examples, however, these examples are non-limitative as there are many such reactions and systems.

1. Alkaline phosphatase-based systems [ALP/AP]: increased levels most consistently associated with liver and bone diseases. Moderate elevations sometimes noted in Hodgkin's disease, congestive heart failure, Fanconi's syndrome, hyperparathyroidism, intestinal disease and intra-abdominal bacterial infections.

2. Acid phosphatase-based systems: increased levels of total and tartrate-inhibited fraction of enzyme associated with prostatic carcinoma that has metastasized. Moderate elevations in total enzyme observed in cases of thromboembolic phenomena, thrombocytopenia, multiple myeloma, liver disease and Paget's disease.

3. Aspartate aminotransferase-based systems [AST/GOT]: increased levels associated with myocardial infarction, becoming evident, 4–6 hours after onset of pain and peaking after 24–36 hours. High levels also observed in cases of liver cell damage, muscular dystrophy and dermatomyositis.

4. Urease-based systems: increased levels associated with renal disease as well as dehydration, diabetic coma, hypoadrenal crisis, gastrointestinal hemorrhage and circulatory collapse. Decreased values observed in some cases of severe liver disease.

5. Glucose oxidase/peroxidase-based systems: increased levels associated with diabetes mellitus, hyperactivity of thyroid, pituitary or adrenal glands. Decreased levels observed in cases of insulin overdosage, insulin secreting tumors, myxedema, hypopituitarism, hypoadrenalism and conditions interfering with glucose absorption.

6. Alcohol dehydrogenase-based systems (NAD): establishes circulating levels of ethanol in cases of suspected intoxication.

As noted, the above systems are only a few examples, and there are, in fact, many systems and reactions which may be used in conjunction with the present invention. Further, although not all reactions are enhanced, they can all be controlled by virtue of the present invention which thereby allows for an increase in accuracy or economical control of labor or machine by exerting greater flexibility over the reaction time.

Additionally, the present invention may be used in conjunction with automated assays using enzymes immobilized on a support.

While it is advantageous to store enzymes and/or reagents to be used in diagnostic enzyme reactions under the present gases, it is particularly advantageous to subject the diagnostic reagents and sample to be analyzed to the present gases and to maintain contact with the gases during the reaction.

Total gas saturation can be achieved in the particular case of an automated analyzer by putting the entire reacting chamber of the apparatus under a noble gas mixture of noble gases or a gas mixture containing at least one noble gas. This will allow to reach the best throughput increase of the said automated analyzer.

The present invention may be used with any diagnostic kit or procedure. Depending on the enzyme, substrate concentration, and temperature the kinetics of the reactions are enhanced or decelerated by contacting the reaction system with the present gases. For example, with hydrolase-based diagnostic kits or procedures, the addition of the present gases result, in enhanced reaction kinetics.

The present invention is also applicable to immobilized-enzyme diagnostics.

Any noble gas will affect the response time of an enzyme-based diagnostic kit or protocol. As used herein, the term "noble gas" means argon, xenon, argon or neon. Helium does not work and radon is radioactive and not useful.

Further, the effects of the present invention on enzyme-based diagnostic systems can be observed on a wide range of pressure, temperature and pH. While in order to measure an effect it is generally only necessary that contact of the present gases occurs with the participants in the biochemical reaction taking place, saturation is generally preferred to obtain the best results.

Contact of the present gases with enzyme activities in either liquid or solid forms may be practiced as similar effects are observed. Contact of the present gases with enzyme activities in other matrices, such as an organic solvent, may also be practiced instead of in aqueous solutions.

Noble gases can affect diagnostic reactions even when in contact with other gases such as oxygen.

As a result of the improved kinetics of the reaction, enzyme-based diagnostic systems can be run at lower temperatures in the presence of noble gases without decreasing their sensitivity.

Further, it is, again, noted that the enhanced control of the reaction time which results permits greater flexibility in manipulation of the reagents and samples and increase the practical utility of the diagnostic systems.

Generally, the present invention may be used in conjuction with any enzyme-based diagnostic systems or procedures, particularly those which are machine operated.

As these procedures are generally conducted in liquid, particularly aqueous media, the following conditions generally apply. Further, although the enzyme reactions are generally conducted in aqueous media, organic media may be used where appropriate. Many enzymes can vigorously function as catalysts in organic solvents. For example, lipases and oxidoreductases are known to function quite well in water-immiscible hydrophobic solvents, such as paraffins, toluene, carbon tetrachloride or chloroform.

In accordance with a preferred aspect of the present invention, it has been discovered to be extremely advantageous to effect a substantial saturation of the medium or media in which the diagnostic enzyme reaction is conducted.

The term "substantially saturate" means that it is not necessary to completely and/or constantly saturate the enzyme reaction environment with said gas or gas mixture (i.e., having the maximum amount of gas solubilized in the reaction medium or media). Usually, it is considered necessary to saturate the reaction medium or media to more than 50% of its (full) saturation level and preferably more than 70%, while 80% or more is considered the most adequate level of saturation of the same. Of course, supersaturation is also possible. This means that if during the progress of the diagnostic enzymatic reaction in the reaction vessel, or other containing means, the reaction medium or media is not saturated with noble gas at least from time to time or even quite longer if it remains generally substantially same rated, results according to the invention are usually obtained. While it is believed that it is important that the entire volume of the container be saturated or substantially saturated with one of the above gas or a mixture thereof, it is quite possible to obtain the results according to the invention if a part of the volume is not saturated during preferably a limited period of time or is less saturated or substantially saturated than other portions of the volume of the reaction space in the container.

While at least one of the above gases must be present in order to obtain the benefits of the invention, said gases can be diluted with some other gases, in order to keep for example the invention economically valuable. Said diluent gases are preferably selected from the group comprising nitrogen, oxygen, nitrous oxide, air, helium or carbon dioxide. In case of an oxygen-containing gas or another reactive gas such as carbon dioxide, their degradative properties are such that these properties will mask the effect of noble gases, certainly in mixtures where they comprise 50% vol. or more and possibly 30% vol. or more. When those mixes comprise 0% to 10% vol. of these other gases, the noble gases referred to above are still extremely effective, while between 10% vol. and 20% vol. they are usually still effective, depending on the type of gases and conditions, which might be easily determined by the man skilled in the art.

In case of nitrogen and/or helium gas, the effect of noble gases consisting of Ar, Ne, Kr, Xe in the mixture is linearly proportional to its concentration in the mixture, which evidences that nitrogen and/or helium have no effect on substantially preventing oxidation. The mixture of noble gas and nitrogen and/or helium can thus comprise any amount (% volume) of nitrogen and/or helium: however, in practice, the lesser the proportion of noble gas selected from the group consisting of Ar, Ne, Kr and Xe, the larger the time required to achieve saturation or substantial saturation of the reaction space.

Among the active gases (Ar, Kr, Xe, and Ne), it is preferred to use argon because it is cheaper than the other active gases. However, mixtures of argon and/or krypton and/or xenon are at least as effective as argon alone. It has also been unexpectedly found that mixtures comprising between 90 to 99% vol. argon and 1 to 10% Xe and/or Kr are usually the most effective as exemplified in the further examples (whether or not they are diluted with nitrogen, helium, or nitrous oxide). The difference in effect between the active gases defined hereabove and nitrogen have been also evidenced by the fact that mixtures of argon and oxygen or carbon dioxide have a similar (while decreased) effect than argon alone, while nitrogen mixed with oxygen or carbon dioxide evidenced no protective or preservative effect compared to oxygen or carbon dioxide alone.

Generally speaking, Xe is the most efficient gas according to the invention, followed by Kr, Ar and Ne. Among the suitable mixes, either pure or diluted with $N_2$, He, $N_2O$ (or even air, oxygen or a small amount of hydrogen) are the Ne/He mix comprising about 50% vol. of each, and the Kr/Xe mix comprising about 5–10% vol. Xe and about 90–95% vol. Kr, with a small amount of argon and/or oxygen (less than 2% vol.) or nitrogen (less than 1% vol.).

The temperatures at which the invention is carried out is usually between about 0° C. to 60° C., and preferably about 10° C. and 30° C.

The injection of the gas or gas mixture into the reaction medium or media and/or into the container, e.g. by sparging is usually done at about 1 atmosphere but is still quite operable at 2 or 3 atmospheres, while saturation is eased at higher pressures. The pressure of the gas above the reaction medium or media in the container shall be, in any case, preferably lower than 10 atmospheres and it is usually acceptable to maintain it lower than 3 atmospheres.

Saturation or substantial saturation of the reaction medium or media can be measured by various methods well-known by the man skilled in the art, including but not limited to thermogravimetric analysis or mass change weighing.

There are a variety of standard methods available for the detection, qualitative and quantitative measurement of gases, and several are especially well suited for the determination of degree of saturation of noble gases into liquid samples.

Samples generally are completely evacuated as a control for zero % saturation. Such samples may then be completely saturated by contact with noble gases such that no additional noble gas will disappear from a reservoir in contact with the sample. Such saturated samples may then have their gas content driven off by trapped evacuation or by increase in temperature, and said gas sample identified quantitatively and qualitatively. Analysis is of trapped gases, reservoir gases, or some other headspace of gases, not directly of the sample.

Direct sample analysis methods are available, and include comprehensive GC/MS analysis, or by mass or thermal conductance or GC analysis and comparison with calibrated standards.

The simplest method is GC/MS (gas chromatography/mass spectrometry), which directly determines gas compositions. By preparing a standard absorption curve into a given sample for a series of gases and mixtures, one can accurately determine the degree of saturation at any point in time.

GC/MS is applied to the gas itself, as in the headspace above a sample. The technique may be used either to determine the composition and quantity of gas or mixture being released from a sample, or conversely the composition and quantity of a gas or mixture being absorbed by a sample by following the disappearance of the gas.

Appropriate GC/MS methods include, for example, the use of a 5 Angstrom porous layer open tubular molecular sieve capillary glass column of 0.32 mm diameter and 25 meter length to achieve separation, isothermally e.g. at 75° C. or with any of several temperature ramping programs optimized for a given gas or mixture e.g. from 35°–250° C., wherein ultra-high purity helium or hydrogen carrier gas is used at e.g. 1.0 cc/min flow rate, and gases are detected based upon their ionicity and quantitative presence in the sample, and characterized by their unique mass spectra.

Appropriate experimental conditions might include, for example, completely evacuating a given sample under vacuum to remove all absorbed and dissolved gases, then adding a gas or mixture to the sample and measuring a) the rate of uptake of each component as disappearance from the added gas, and/or b) the final composition of the gas headspace after equilibration. Both measurements are made by GC/MS, and either method can be used in both batch and continuous modes of operation.

A simplification of this analysis entails the use of a GC only, with a thermal conductivity detector, wherein adequate knowledge of the gas saturation process and preparation of calibration curves have been made such that quantification and characterization of gases and mixtures can be accomplished without mass spectral analysis. Such instruments are relatively inexpensive and portable. A further simplification would depend solely upon measurement of the mass change in the sample upon uptake of various gases or mixtures, which depends upon the use of standard curves or absorption data available from the literature.

An alternate method for such mass measurements is thermogravimetric analysis, which is highly precise, wherein a sample is saturated with gas and mass changes are correlated to thermal change.

Having generally described the present invention, the same will now be further illustrated by reference to certain examples which are provided purposes of illustration and which are not intended to be limitative.

EXAMPLE 1

Alkaline Phosphatase [ALP/AP] Sigma Kit. No. 245-10 Gas Run Protocol

Phosphatase, Alkaline P-8008

(Orthophosphoric-monoester phosphohydrolase [alkaline optimum]; EC 3.1.3.1)

Unit Definition: One unit will hydrolyze 1.0 µmole of p-nitrophenyl phosphate per min at pH 10.4 at 37° C.

Type V

From Chicken Intestine 5.1 Units/mg solid (1 g solid) Lot# 115F-3806

SIGMA Diagnostic Kit 245-10 (Procedure No. 245)
SUBSTRATE
Alkaline Phosphatase [ALP] reagent
When reconstituted with 10.0 ml D.I. H$_2$O per vial, contains approximately:

| p-Nitrophenyl Phosphate | 16 mmol/L |
| Magnesium ions | 4 mmol/L |
| Mannitol | 274 mmol/L |
| Buffer | pH 10.2 ± 0.1 |

Lot# 118F-6158
DILUTENT
221 Alkaline Buffer Solution (Sigma No. 221)
2-Amino-2-methyl-1-propanol buffer, 1.5 mol/L, pH 10.3 at 25° C. Lot# 59F-6109
PRINCIPLE

p-Nitrophenyl Phosphate + H$_2$O $\xrightarrow{\text{ALP}}$ p-Nitrophenol + Phosphate The hydrolysis occurs at alkaline pH. The formation of p-nitrophenol can be observed as an increase in absorbance at 405 nm. The rate of increase directly proportional at ALP activity.

KIT CALIBRATION PROCEDURE

Total volume in cuvette: 1.02 ml
20 µL ALP solution with a linearity top limit of 1,200 U/L
1 ml ALP reagent
Enzyme/Substrate content per cuvette:
Alkaline Phosphatase (Linearity top limit): 0.0240 Units
p-Nitrophenyl Phosphate: 16 µmol
Enzyme/Substrate concentrations in cuvette (V$_{tot}$=1.02 ml):
Alkaline Phosphatase (Linearity top limit): 0.0235 U/ml
p-Nitrophenyl Phosphate: 15.7 µmol/ml
Gas Run Concentrations
Substrate Concentration

| Alkaline Phosphatase Solution B (0.1 U/Mi) [ml] | p-Nitrophenyl Phosphate Solution C (ALP reagent) [ml] |
|---|---|
| 0.5 | 2 |

Enzyme/Substrate content per cuvette:
Alkaline Phosphatase: 0.050 Units
p-Nitrophenyl Phosphate: 32 µmol
Enzyme/Substrate concentrations in cuvette (V$_{tot}$=2.5 ml):
Alkaline Phosphatase: 0.02 U/ml
p-Nitrophenyl Phosphate: 12.8 µmol/ml
PARAMETERS

| Gaseous atmospheres: |
|---|
| G1 Air |
| G2 90% Kr/10% Xe |
| G3 Argon |
| G4 Krypton |
| G5 Xenon |
| G6 Oxygen O$_2$ |
| G7 Nitrogen N$_2$ |
| G8 Air |
| G9 Ne |
| G10 SF$_6$ |
| Temperatures: |
| T1 10° C. |
| T2 25° C. |
| T3 35° C. |
| Blank: |
| R = 2.0 ml Soln C + 0.5 ml Soln A |

SOLUTION PREPARATION

Soln A: 221 Alkaline Buffer Solution (Sigma No. 221), pH 10.3 at 25° C.
Use solution as purchased.
Soln B: Alkaline phosphatase (Sigma No. P-S8008), 1 u/ml
Dissolve 10 mg P-8008 in 50 ml Soln A.
Soln C: ALP Reagent: p-Nitrophenyl phosphate Reconstitution of 8 ALP vials according to the directions (Procedure No. 245) with 80 ml D.I. H$_2$O.

| p-Nitrophenyl Phosphate | 16 mmol/L |
| Magnesium ions | 4 mmol/L |

-continued

| | |
|---|---|
| Mannitol | 274 mmol/L |
| Buffer | pH 10.2 ± 0.1 |

Stored at 0°–5° C. in an amber bottle.

SOLUTION TESTING

TDrive, 405 run, 35° C., 40 pts, 15 s
S = 2.0 ml Soln C + 0.5 ml Soln B
R = 2.0 ml Soln C + 0.5 ml Soln A

24515S5.SP

Materials Needed
Siliconed acrylic cuvettes: 10×3 (G×T)

$$\begin{array}{r} 10 \times 3 \quad (G \times T) \\ \underline{1 \quad (P2)} \\ 31 \text{ cuvettes} \end{array}$$

221 Buffer Solution, pH 10.3 (25° C.): 151 ml
ALP Reagent solution: 62 ml
Alkaline phosphatase solution F1/10 (0.1 U/ml): 50 ml
Serum vials (10 cc): 10 (5 ml/each)
Needles: B-D 20G½
Label silicone-sealed cuvettes (P2T?G?)

PROCEDURE

Purge cuvettes with air (3×10 cc)
Fill the cuvettes with 2 ml of Soln C with a 1 cc syringe.
Keep cuvettes in refrigerator in the dark.
Fill 10 cc serum vials with Soln B.
Keep serum vials in refrigerator.
Spectrophotometer set-up:

| PARAM: | ABS |
|---|---|
| | slit 1 nra |
| | speed 1,500 nm/min |
| | Asave Y |
| | Aprnt N |
| Background correction: | 900–190 nm |

T3 RUNS (35° C.)

| CPRG | 5 cells | |
|---|---|---|
| | 405 nm | |
| | Pts 40 | ===> 10 min RUN |
| | int 15 | |
| | $Y_{min} = 0.0$ | |
| | $Y_{max} = 4.0$ | |

Set Digital controller on 35° C. and Fisher circulator on 30° C. and high pump speed.

Remove the T3G1 . . . 5 cuvettes from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T3G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.1 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T3,P2)      10min

Remove the T3G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T3G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.1 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T3,P2)      10min

T2 RUNS (25° C.)

| CPRG | 5 cells | |
|---|---|---|
| | 405 nm | |
| | Pts 60 | ===> 15 min RUN |
| | int 15 | |
| | $Y_{min} = 0.0$ | |
| | $Y_{max} = 4.0$ | |

Set Digital controller at 25° C. and the Fisher circulator on 20° C., and high pump speed).

Remove the T2G1 . . . 5 cuvettes from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T2G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.1 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T2,P2)      15min

Remove the T2G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T2G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.1 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T2,P2)    15min

T1 RUNS (10° C.)

---
CPRG    5 cells
        405 nm
        Pts 60        ===> 15 min RUN
        int 15
        $Y_{min} = 0.0$
        $Y_{max} = 4.0$
---

Set Digital controller at 10° C. and the Fisher circulator on 5° C., and high pump speed). Hook $N_2$ to spectrophotometer and have a continuous flow of 20 psi throughout the experiment to prevent condensation on the outside of the cuvettes.

Remove the T1G1 . . . 5 cuvettes from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T1G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.1 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T1,P2)    20min

Remove the T1G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T1G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.1 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T1,P2)    20min

---
SPECTRA FILES:
P2T3G1 . . . 5.SP
P2T3G6 . . . 0.SP
P2T2G1 . . . 5.SP
P2T2G6 . . . 0.SP
P2T1G1 . . . 5.SP
P2T1G6 . . . 0.SP
30 FILES
---

EXAMPLE 2
Acid Phosphatase Sigma Kit. No. 435-A Gas Run Protocol

ENZYME

Phosphatase, Acid P-3752
(Orthophosphoric-monoester phosphohydrolase [acid optimum)]; EC 3.1.3.2)

Unit Definition: One unit will hydrolyze 1.0 μmole of p-nitrophenyl phosphate per min at pH 4.8 at 37° C. Type II From Potato 0.8 Units/mg solid (1 g solid) Lot# 17F-7285

SIGMA Diagnostic Kit 435-A (Procedure No. 435)

SUBSTRATE

Acid Phosphatase [ACP] reagent

When reconstituted with 10.0 ml D.I. $H_2O$ per vial, contains:

---
| α-Naphthyl Phosphate | 4 mmol/L |
| Fast Red TR | 1 mmol/L |
| Buffer | pH 5.0 ± 0.1 |
| Nonreactive stabilizers and fillers | |
| Lot# 29F-6030 | |
---

DILUTENT

Citrate Buffer Solution (Sigma No. 104-4)

Citrate 90 mmol/L, and chloride 10 mmol/L, pH 4.8 at 25° C.

Contains chloroform as a preservative Lot# 58F-6146

PRINCIPLE

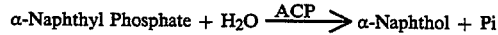

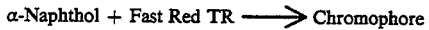

Acid phosphatase [ACP] catalyzes the hydrolysis of α-Naphthyl phosphate to a-Naphthol and inorganic phosphate. α-Naphthol immediately reacts with fast red TR salt to produce a yellow chromophore with an absorbance maximum at 405 nm. The rate of increase in absorbance at 405 nm is directly proportional to ACP activity.

KIT CALIBRATION PROCEDURE

Total volume in cuvette: 1.1 ml 0.1 ml Acid phosphatase solution with a linearity top limit of 40 Units/L 1 ml [ACP] Reagent Enzyme/Substrate content per cuvette:

Acid phosphatase (Linearity top limit): 0.004 Units

α-Naphthyl phosphate: 4 μmol

Enzyme/Substrate concentrations in cuvette ($V_{tot}=1.1$ ml):

Acid phosphatase (Linearity top limit): 0.0036 U/ml

α-Naphthyl phosphate: 3.6 μmol/ml

Gas Run Concentrations

---
| Substrate Concentration: | |
| --- | --- |
| Acid Phosphatase | α-Naphthyl Phosphate |
| solution | solution |
| Reagent A | Reagent B5/5 |
| (0.32 U/ml) | (ACP reagent) |
---

-continued

| [ml] | [ml] |
|---|---|
| 0.5 | 2 |

===> Enzyme/Substrate content per cuvette:
Acid Phosphatase: 0.16 Units
a-Naphthyl Phosphate: 8 Amol
===> Enzyme/substrate concentrations in cuvette ($V_{tot}$ = 2.5 ml):
Alkaline Phosphatase: 0.064 U/ml
a-Naphthyl Phosphate: 3.2 ymol/ml

PARAMETERS

Gaseous atmospheres:
G1 Air
G2 90% Kr/10% Xe
G3 Argon
G4 Kryton
G5 Xenon
G6 Oxygen $O_2$
G7 Nitrogen $N_2$
G8 Air
G9 Ne
G10 $SF_6$ Temperatures:
T1 10° C.
T2 20° C.
T3 35° C.

Blank:
R = 2.0 ml B5/5 + 0.5 ml Citrate Buffer Solution

SOLUTION PREPARATION
Soln A: Citrate Buffer Solution (Sigma No. 104-4)
Use solution as purchased.
Soln B: Acid phosphatase (Sigma No. P-3752), 0.32 U/ml
Dissolve 20 mg P-3752 in 50 ml Soln A. Store at 05° C. in amber bottle.
Soln C: ACP reagent, α-Naphthol phosphatase
Reconstitute 8 vials according to the directions (Procedure No. 435) with 80 ml D.I. $H_2O$:

| α-Naphthyl Phosphate | 4 mmol/L |
|---|---|
| Fast Red TR | 1 mmol/L |
| Buffer | pH 5.0 ± 0.1 |
| Nonreactive stabilizers and fillers | |

Store at 0°–5° C. in an amber bottle.
SOLUTION TESTING

TDrive, 405 nm, 35° C., 120 pts, 15 s
S = 2.0 ml Soln C + 0.5 ml Soln B
R = 2.0 ml Soln C + 0.5 ml Soln A

4358S5.SP

Materials Needed
Siliconed acrylic cuvettes:

10 × 3(G × T)
1        (P3)
---
31 cuvettes

Citrate Buffer Solution, pH 4.8 (25° C.): 151 ml
ACP Reagent, Solution C: 62 ml
Acid phosphatase: Solution B (0.32 U/ml): 50 ml
Serum vials (10 cc): 10 (5 ml/each)
Needles: B-D 20G½
PROCEDURE Label silicone-sealed cuvettes (P3T?G?)
Purge cuvettes with air (3×10 cc)
Fill the cuvettes with 2 ml of ACP reagent Soln C with 1 cc syringe.
Keep cuvettes in refrigerator in the dark.
Fill 10 cc serum vials with Acid phosphatase Solution B (0.32 U/ml).
Keep serum vials in refrigerator.
Spectrophotometer set-up:

| PARAM: | ABS |
|---|---|
|  | slit 1 nm |
|  | speed 1,500 nm/min |
|  | Asave Y |
|  | Aprnt N |

T3 RUNS (35° C.)

| CPRG | 5 cells | |
|---|---|---|
|  | 405 nm | |
|  | Pts 60 | ===> 30 min RUN |
|  | int 15 | |
|  | $Y_{min}$ = 0.0 | |
|  | $Y_{max}$ = 4.0 | |

Set Digital controller on 35° C. and Fisher circulater on 30° C. and high pump speed.
Remove the T3G1 . . . 5 cuvettes from the refrigerator. Bubble 6×10 cc of the appropriate gas. Return cuvettes to refrigerator (under two 10 cc syringes).
Remove G1 . . . 5 vials from the refrigerator. Bubble 8×10 cc of the appropriate gas. Return vials to refrigerator (under two 10 cc syringes).
Remove T3G1 . . . 5 cuvette from refrigerator. Remove syringes from cuvette. Tap cuvettes to eliminate bubbles. Wipe walls. Put cuvettes in cell holder.
Remove G1 . . . 5 vials from refrigerator. Sample Soln B (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T3,P3)                     30min

Remove the T3G6 . . . 0 cuvettes from the refrigerator. Bubble 6×10 cc of the appropriate gas. Return cuvettes to refrigerator (under two 10 cc syringes).
Remove G6 . . . 0 vials from the refrigerator. Bubble 8×10 cc of the appropriate gas. Return vials to refrigerator (under two 10 cc syringes).
Remove T3G6 . . . 0 cuvettes from refrigerator. Remove syringes from cuvettes. Tap cuvettes to eliminate bubbles. Wipe walls. Put cuvettes in cell holder.
Remove G6 . . . 0 vials from refrigerator. Sample Soln B solution (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T3,P3)                     30min

T2 RUNS (25° C.)

| CPRG | 5 cells |
|---|---|
|  | 405 nm |

-continued

| | |
|---|---|
| Pts 120 | ===> 30 min RUN |
| int 15 | |
| $Y_{min} = 0.0$ | |
| $Y_{max} = 4.0$ | |

Set Digital controller at 25° C. and the Fisher circulator on 20° C., and high pump speed).

Remove the T2G1 . . . 5 cuvettes from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T2G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T2,P3)    30min

Remove the T2G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T2G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,Gg, G0],T2,P3)    30min

T1 RUNS (10° C.)

| CPRG | 5 cells | |
|---|---|---|
| | 405 nm | |
| | Pts 120 | ===> 30 min RUN |
| | int 15 | |
| | $Y_{min} = 0.0$ | |
| | $Y_{max} = 4.0$ | |

Set Digital controller at 10° C. and the Fisher circulator on 5° C., and high pump speed). Hook N2 to spectrophotometer and have a continuous flow of 20 psi throughout the experiment to prevent condensation on the outside of the cuvettes.

Remove the T1G1 . . . 5 cuvettes from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T1G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T1,P3)    30min

Remove the T1G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T1G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T1,P3)    30min

| SPECTRA FILES: |
|---|
| P3T3G1 . . . 5.SP |
| P3T3G6 . . . 0.SP |
| P3T2G1 . . . 5.SP |
| P3T2G6 . . . 0.SP |
| P3T1G1 . . . 5.SP |
| P3T1G6 . . . 0.SP |
| 30 FILES |

EXAMPLE 3

Aspartate Aminotransferase [AST/GOT] Kit No. 58-10 Gas Run Protocol

ENZYME

Aspartate Aminotransferase G-7005

(Glutamic-Oxalacetic Transaminase; GOT; L-aspartate: 2-oxoglutarate aminotransferase; EC 2.6.1.1)

UNIT DEFINITION: One unit will convert 1.0 μmole of α-keto-glutarate to L-glutamate per min at pH 7.5 at 37° C. in the presence of L-aspartic acid. one unit is equivalent to approx. 2000 OD (Karmen) units at 25° C. Protein determined by Biuret.

Type II-A: From Porcine heart; lypholized powder containing approx. 85% protein and approx. 15% buffer salt as sodium citrate. 1.7 mg solid 308 units/mg solid 385 units/mg protein 524 units Lot No. 127F-9645 Store desiccated at 0° C.

Sigma Diagnostic Kit AST 58-10 (Procedure No. 58-UV)

SUBSTRATE

Aspartate Aminotransferase [AST/GOT] reagent

When reconstituted according to the directions (10 ml D. I. H2O per vial), contains the following concentrations of active ingredients:

| | |
|---|---|
| L-Aspartate | 200 mmol/L |
| 2-Oxoglutarate | 12 mmol/L |
| MD [Porcine] | 600 U/L |
| NADH | 0.2 mmol/L |

| | |
|---|---|
| Buffer | pH 7.8 ± 0.1 |
| Nonreactive stabilizers and fillers | |

Store in refrigerator (2°-6° C.).
DILUENTS
Deionized H₂O.
0.1M Sodium Phosphate buffer, pH 7.5
PRINCIPLE L-Aspartate + 2-Oxoglutarate $\xrightarrow{AST}$ Oxalacetate + L-Glutamate Oxalacetate + NADH $\xrightarrow{MD}$ L-Malate + NAD AST catalyzes the transfer of the amino group from aspartate to 2-oxoglutarate to yield oxalacetate and glutamate. The oxalacetate is reduced to malate in the presence of malate dehydrogenase [MD] with the simultaneous oxidation of reduced nicotinamide adenine dinucleotide [NADH]. The rate of decrease in absorbance at 340 nm is directly proportional to AST activity.

CALIBRATION PROCEDURE
SIGMA PROCEDURE:
Total volume in cuvette: 1.1 ml
0.1 ml Aspartate aminotransferase (glutamic oxalacrtic transaminase); Linearity top limit of 450 U/L.
1.0 ml [AST/GOT] Reagent
Enzyme/Substrate content per cuvette:

| | |
|---|---|
| Aspartate aminotransferase [GOT] (Linearity top limit): | 0.045 units |
| [AST/GOT] Reagent: | |
| L-Aspartate | 200 μmol |
| 2-Oxoglutarate | 12 μmol |
| MD (Porcine) | 0.6 units |
| NADH | 0.2 μmoles |

Enzyme/Substrate concentrations in cuvette (V$_{tot}$=1.1 ml):

| | |
|---|---|
| Aspartate aminotransferase [GOT] (Linearity top limit): | 0.041 units/ml |
| [AST/GOT] Reagent: | |
| L-Aspartate | 200 μmol/ml |
| 2-Oxoglutarate | 12 μmol/ml |
| MD (Porcine) | w 7 7@ its/ml |
| NADH | 0.18 μmol/ml |

TESTING PROCEDURE
Total volume in cuvette: 2.5 ml
0.5 ml Aspartate aminotransferase (glutamic oxalacetic transaminase) Linearity top limit of 0.18 units/ml.
2 ml [AST/GOT] Reagent
Enzyme/Substrate content per cuvette:

| | |
|---|---|
| Aspartate aminotransferase [GOT] (Linearity top limit): | 0.09 units |
| [AST/GOT] Reagent: | |
| L-Aspartate | 400 μmol/ml |
| 2-Oxoglutarate | 24 μmol/ml |
| MD (Porcine) | 1.2 units |
| NADH | 0.4 μmoles |

Enzyme/Substrate concentrations in cuvette (V$_{tot}$=2.5 ml):

| | |
|---|---|
| Aspartate aminotransferase [GOT] (Linearity top limit): | 0.036 units/ml |
| [AST/GOT] Reagent: | |
| L-Aspartate | 160 μmol/ml |
| 2-Oxoglutarate | 9.6 μmol/ml |
| MD (Porcine) | 0.48 units/ml |
| NADH | 0.16 μmol/ml |

PARAMETERS

| |
|---|
| GASEOUS ATMOSPHERES: |
| G1 AIR (G8) |
| G2 90% Kr/10% Xe |
| G3 ARGON |
| G4 KRYPTON |
| G5 XENON |
| G6 OXYGEN O₂ |
| G7 NITROGEN N₂ |
| G8 AIR |
| G9 NEON |
| TEMPERATURES: |
| T1 10° C. |
| T2 25° C. |
| T3 35° C. |

SOLUTION PREPARATION: Jul. 18, 1990
Soln A: 0.1M Sodium Phosphate buffer, pH 7.5
Dissolve 5.96 g Na₂HPO₄ and 0.96 g NaH₂PO₄ in 1 liter of D.I. H₂O. Adjust pH.
Soln B0: Aspartate aminotransferase [Glutamic oxalacetic transaminase] G=7005, 5.2 U/ml
Transfer the contents of the bottle (1.7 mg) of G-7005 with soln A. Dilute to 100 ml with Soln A. Stored in refrigerator (0°-5° C.) in an amber bottle.
Soln B1: Aspartate aminotransferase [Glutamic oxalacetic transaminase] G-7005, 1.8 U/ml
Dilute 35 ml of Soln B0 to 100 ml with Soln A.
Stored in refrigerator (0°-5° C.) in an amber bottle.
Soln B2: Aspartate aminotransferase [Glutamic oxalacetic transaminase] G-7005, 0.18 U/ml
Dilute 10 ml of Soln B1 to 100 ml with soln A.
Stored in refrigerator (0°-5° C.) in an amber bottle.
Soln C1: [AST/GOT] Reagent:
Reconstitute 6 [AST/GOT] Reagent vials according to the directions on the vial: 10.0 ml D.I. H₂O in each vial.

| | |
|---|---|
| Aspartate | 200 mmol/L |
| 2-Oxoglutarate | 12 mmol/L |
| MD [Porcine] | 600 U/L |
| NADH | 0.1 mmol/L |
| Buffer | pH 7.8 ± 0.1 |

NOTE: MIX BY INVERSION. DO NOT SHAKE.

Soln C2: [AST/GOT] Reagent:
Reconstitute 6 [AST/GOT] Reagent vials according to the directions on the vial: 5.0 ml D.I. H₂O in each vial.
The [AST/GOT] reagents (Solutions C1 and C2) are not suitable for use if the absorbance of freshly reconstituted solution measured in a 1-cm path at 340 nm versus water as reference is below 0.800.

SOLUTION TESTING: Jul. 19, 1990
35° C.
TDrive, 335 nm, 40 pts, 15 s int. (10 min):
S=2.0 ml Soln C+0.5 ml Soln B
R=2.5 ml H$_2$O
Materials Needed
Siliconed acrylic cuvettes $$\begin{array}{r} 9 \times 3(G \times T) \\ \underline{1 \quad \quad (J9)} \\ 29 \quad \text{cuvettes} \end{array}$$

[AST/GOT] Reagent solution: 58 ml
Aspartate Aminotransferase [GOT] solution A35/500 (0.18 U/ml): 45 ml
Serum vials (10 cc): 9 (5 ml/each)
Needles BD 20G½
PROCEDURE
Label silicone-sealed cuvettes (J9T?G?)
Purge cuvettes with air (3×10 cc)
Fill the cuvettes with 2 ml of Solution C using a 1 cc syringe
Keep cuvettes in refrigerator in the dark.
Fill 10 cc serum vials with 5 ml of Solution B2 (0.18 units/ml).
Wrap serum vials containing the enzyme solution with aluminum foil to prevent light degradation of the enzyme.
Spectrophotometer set-up:

| PARAM: | ABS |
|---|---|
| | slit 1 nm |
| | speed 1,500 nm/min |
| | Asave Y |
| | Aprnt N |

Gas run
Jul. 20, 1990
T1 RUNS (10° C.):

| CPRG | 5 cells, 4 cells |
|---|---|
| | 335 nm |
| | 80 pts, 20 min |
| | int 15 |
| | $y_{min}$ = 0.0 |
| | $y_{max}$ = 2.0 |

Set Digital controller at 10° C. and the Fisher circulator on 5° C., and high pump speed). Hook N$_2$ to spectrophotometer and have a continuous flow of 20 psi throughout the experiment to prevent condensation on the outside of the cuvettes.

Remove the T1G1 . . . 5 cuvette from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T1G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T1,P3)  30min

Remove the T1G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T1G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T1,P3)  30min

T2 RUNS (25° C.)

| CPRG | 5 cells, 4 cells |
|---|---|
| | 335 nm |
| | 60 pts, 15 min |
| | int 15 |
| | $y_{min}$ = 0.0 |
| | $y_{max}$ = 2.0 |

Set Digital controller at 25° C. and the Fisher circulator on 20° C., and high pump speed).

Remove the T2G1 . . . 5 cuvettes from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T2G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T2,P3)  30min

Remove the T2G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T2G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T2,P3)  30min

T3 RUNS (35° C.)

| CPRG | 5 cells, 4 cells |
|---|---|
| | 335 nm |
| | 40 pts, 10 min |
| | int 15 |
| | $y_{min} = 0.0$ |
| | $y_{max} = 2.0$ |

Set Digital controller on 35° C. and Fisher circulator on 30° C. and high pump speed.

Remove the T3G1 . . . 5 cuvettes from the refrigerator. Bubble 6×10 cc of the appropriate gas. Return cuvettes to refrigerator (under two 10 cc syringes).

Remove G1 . . . 5 vials from the refrigerator. Bubble 8×10 cc of the appropriate gas. Return vials to refrigerator (under two 10 cc syringes).

Remove T3G1 . . . 5 cuvettes from refrigerator. Remove syringes from cuvettes. Tap cuvettes to eliminate bubbles. Wipe walls. Put cuvettes in cell holder.

Remove G1 . . . 5 vials from refrigerator. Sample Soln B (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G1,G2,G3,G4,G5],T3,P3)    30min

Remove the T3G6 . . . 0 cuvettes from the refrigerator. Bubble 6×10 cc of the appropriate gas. Return cuvettes to refrigerator (under two 10 cc syringes).

Remove G6 . . . 0 vials from the refrigerator. Bubble 8×10 cc of the appropriate gas. Return vials to refrigerator (under two 10 cc syringes).

Remove T3G6 . . . 0 cuvettes from refrigerator. Remove syringes from cuvettes. Tap cuvettes to eliminate bubbles. Wipe walls. Put cuvettes in cell holder.

Remove G6 . . . 0 vials from refrigerator. Sample Soln B solution (0.32 U/ml) with 1 cc syringes previously filled with the appropriate gas, push syringes thru silicone plugs but not into the solution. Simultaneously push syringes fully into the cuvettes then simultaneously push plungers. Start CPRG.

([G6,G7,G8,G9,G0],T3, P3)    30min

| SPECTRA FILES: |
|---|
| J9T1G1 . . . 5.SP |
| J9T1G6 . . . 9.SP |
| J9T2G1 . . . 5.SP |
| J9T2G6 . . . 9.SP |
| J9T3G1 . . . 5.SP |
| J9T3G6 . . . 9.SP |
| 27 FILES |

EXAMPLE 4

Urea Nitrogen Diagnostic Kit (640) Protocol For Gas Run

Urea Nitrogen (Sigma Diagnostic Kit, Procedure No. 640)
  Phenol Nitroprusside Solution
    Sigma No. 640-1 Phenol, 50 g/L, sodium nitroprusside and stabilizer. Store in refrigerator. Note expiration date: AUGUST 1993
  DANGER: causes burns. Do not get in eyes, on skin or clothing.
  Alkaline Hypochlorite Solution
    Sigma Mo. 640-3 Sodium hypochlorite, 0.2%, in alkali. Store in refrigerator. Note expiration date: OCTOBER 1993
  DANGER: causes burns. Do not get in eyes, on skin or clothing.
  Urease Buffer Reagent, Dry Vial,
    Sigma No. 640-5 Buffered Urease from jack beans 100 units when prepared according to directions (3.33 units/ml). Sodium azide added as preservative. Store in refrigerator. Note expiration date: JUNE 1993
  WARNING: contains sodium azide which may react with lead and copper plumbing to form highly explosive metal azides. On disposal, flush with a large volume of water to prevent azide accumulation.
  Urease Solution is prepared by reconstituting vial of Urease Buffer Reagent with 30 ml water. Stable at least 1 month when refrigerated. Avoid contact with skin or mouth.
  Urea Nitrogen Standard Solution 1
    Sigma No. 535-30 Urea at a urea N level of 30 mg/dl [10.7 mmol/L] and benzoic acid as preservative. Store in refrigerator. Note expiration date: SEPTEMBER 1993
  Urea Nitrogen Standard Solution 2
    Sigma No. 535-150 Urea at a urea N level of 150 mg/dl [53.3 mmol/L] and benzoic acid as preservative. Store in refrigerator. Note expiration date: MAY 1994

PRINCIPLE: Urea is hydrolyzed by urease to ammonia and carbon dioxide.

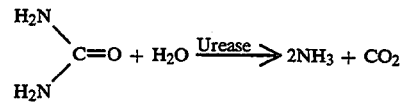

Ammonia then reacts with alkaline hypochlorite and phenol in the presence of a catalyst, sodium nitroprusside [Na$_2$Fe[CN]$_5$NO.2H$_2$O], to form indophenol. The concentration of ammonia is directly proportional to the absorbance of indophenol, which is measured spectrophotometrically at 570 nm.

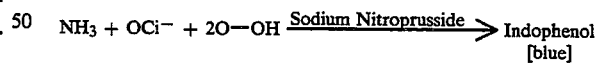

Note: Ammonia free water (DI H$_2$O should be ok) is necessary for this procedure, Make sure to rinse everything with DI H$_2$O before use, If the blank has more than a trace of blue color ammonia contamination should be suspected.

Materials Needed:
  7×100 cc serum vials, stoppers, seals and crimper
  7×3 cc serum vials, stoppers, seals and crimper
  7×15×10 cc serum vials 500 ml gas-tight Hamilton syringe
  10 cc syringes
  5 cc syringes
  1 cc syringes
  1 ml pipets
  stop watch
  Solution Preparation Soln A: Urease (3.33 U/ml)
Reconstitute 1 vial of Urease Buffer
reagent with 30 ml DI H$_2$O.
Soln A1: Urease (1 U/ml)
Dilute 9 ml of Soln A to 30 ml with D.I. H$_2$O.
Soln B: Blank Soln
4.9 ml of Soln A
0.1 ml Urea Nitrogen Standard (approx 0.098 ml)
10 ml Phenol nitroprusside
10 ml alkaline hypochlorite
50 ml H$_2$O

PROCEDURE FOR STOP-FLOW GAS EXPERIMENT

Prepare 15×10 cc serum vials. Fill each vial with 1 ml Phenol Nitroprusside. Label the vials from 1–15.

Prepare 15×5 cc syringes. Fill each syringe with 5 ml D.I. H$_2$O.

Prepare 15×1 cc syringes. Fill each syringe with 1 ml Alkaline Hypochlorite Solution (Sigma No. 640-3)

In a 100 cc serum vial place 20 ml Urease soln (Soln A1). Stopper, seal and crimp. Bubble 400 ml of gas through (using the 500 ml gas-tight syringe). Superimpose 100 ml of gas, vial will be under positive pressure.

In a 3 cc serum vial place 0.8 ml Urea Nitrogen Standard Solution 1 (Sigma No. 535-30; urea N 30 mg/dl; lot No. 80H-6286). Bubble 4×10 ml of gas through (using 10 cc syringes).

Fill 15 1 cc syringes with gas to be ready for sampling of urea/urease mix.

Sample 0.4 ml Urea Nitrogen Standard Solution 1 from gassed 3 cc vial. Add to the gassed 100 cc serum vial (containing 20 ml Soln A1). Start stop watch, gently swirl vial.

Take 0.5 ml samples every minute. Place the 0.5 ml sample into the corresponding 10 cc vial to stop the reaction. Inject immediately 1 ml Alkaline Hypochlorite Solution followed by 5 ml D.I. H$_2$O.

Continue taking samples for 15 minutes total.

Let the 15×10 cc vials sit and develop color for 30 minutes. a 1 wavelength "scan" (see software) should be run: 3 ml per cuvette. Read vs a blank of 3 ml Soln B.

For each gas studied:
Fill reference cuvette with 2.5 ml Soln B
After 30 min (color development), remove 2.5 ml from each 10 cc vial and place in a cuvette.
Read each cuvette vs R=2.5 ml Soln B

| PECSS command: | WAVEPROGRAM |
| --- | --- |
| | 3 cycles |
| | 0.5 s time interval |
| | 1 wavelength 635 nm |

Spectrophotometric study procedure: 25° C.
Filenames:
Gas=Air G1 Filename UG1T1S01.WP Cell 1-5 vial 1 min-5 min Filename UG1T1S16.WP Cell 1-5 vial 6 min-10 min Filename UG1T1S31.WP Cell 1-5 vial 11 min-15 min
Gas=Nitrogen G2 Filename UG2T1S01.WP Cell 1-5 vial 1 min-5 min Filename UG2T1S16.WP Cell 1-5 vial 6 min-10 min Filename UG2T1S31.WP Cell 1-4 vial 11, 12, 13, 15 min
Gas=Argon G3 Filename UG3T1S01.WP Cell 1-5 vial 1 min-5 min Filename UG3T1S16.WP Cell 1-3 vial 6 min-8 min Filename UG3T1S25.WP Cell 1-5 vial 11 min-15 min
Gas=Krypton G4 Filename UG4T1S01.WP Cell 1-4 vial 1, 3, 4, 5 min Filename UG4T1S13.WP Cell 1-5 vial 6 min-10 min Filename UG4T1S28.WP Cell 1-5 vial 11 min-15 min
Gas=Xenon G5 Filename UG5T1S01.WP Cell 1-5 vial 1, 3, 4, 5, 6 min Filename UG5T1S16.WP Cell 1-5 vial 7 min-11 min Filename UG5T1S31.WP Cell 1-4 vial 12 min-15 min
Gas=Oxygen G6 Filename UG6T1S01.WP Cell 1-5 vial 1 min-5 min Filename UG6T1S16.WP Cell 1-5 vial 6 min-10 min Filename UG6T1S31.WP Cell 1-4 vial 11, 13, 14, 15 min
Gas=Neon G7 Filename UG7T1S01.WP Cell 1-5 vial 1 min-5 min Filename UG7T1S16.WP Cell 1-5 vial 6 min-10 min Filename UG7T1S31.WP Cell 1-4 vial 11, 12, 13, 15 min
Gas=Argon (redo) E3 Filename UE3T1S01.WP Cell 1-5 vial 1 min-5 min Filename UE3T1S16.WP Cell 1-5 vial 6 min-10 min Filename UE3T1S31.WP Cell 1-5 vial 11 min-15 min RESULTS HAVE BEEN ENTERED IN A LOTUS MATRIX: UREAT1.WK3 (Disk Urease'92).

Spectrophotometric study procedure: 37° C.
Filenames:
Gas=Air G1 Filename UG1T2S01.WP Cell 1-5 vial 1 min-5 min Filename UG1T2S16.WP Cell 1-5 vial 6 min-10 min
Gas=Nitrogen G2 Filename UG2T2S01.WP Cell 1-5 vial 1 min-5 min Filename UG2T2S16.WP Cell 1-5 vial 6 min-10 min
Gas=Argon G3 Filename UG3T2S01.WP Cell 1-5 vial 1 min-5 min Filename UG3T2S16.WP Cell 1-3 vial 6 min-10 min
Gas=Krypton G4 Filename UG4T2S01.WP Cell 1-5 vial 1-5 min Filename UG4T2S16.WP Cell 1-5 vial 6 min-10 min
Gas=Xenon G5 Filename UG5T2S01.WP Cell 1-5 vial 1-5 min Filename wHGHUG502S16.WP Cell 1-5 vial 6-10 min
Gas=Oxygen G6 Filename UG6T2S01.WP Cell 1-5 vial 1 min-5 min Filename UG6T2S16.WP Cell 1-5 vial 6 min-10 min
Gas=Neon G7 Filename UG7T2S01.WP Cell 1-5 vial 1 min-5 min Filename UG7T2S16.WP Cell 1-5 vial 6 min-10 min RESULTS HAVE BEEN ENTERED IN A LOTUS MATRIX: UREAT2.WK3 (Disk Urease'92).

Spectrophotometric study procedure: 10° C.
Filenames:
Gas=Air G1 Filename UG1T1S41.WP Cell 1-5 vial 1 min-5 min Filename UG1T1S56.WP Cell 1-5 vial 6 min-10 min Filename UG1T1S71.WP Cell 1-5 vial 11 min-15 min
Gas=Nitrogen G2 Filename UG2T3S01.WP Cell 1-5 vial 1 min-5 min Filename UG2T3S16.WP Cell 1-5 vial 6 min-10 min Filename UG2T3S31.WP Cell 1-5 vial 11 min-15 min Filename UG2T3S46.WP Cell 1-5 vial 16 min-20 min
Gas=Argon G3 Filename UG3T3S01.WP Cell 1-5 vial 1 min-5 min Filename UG3T3S16.WP Cell 1-5 vial 6 min-10 min Filename UG3T3S25.WP Cell 1-5 vial 11 min-15 min Filename UG3T3S41.WP Cell 1-5 vial 16 min-20 min
Gas=Krypton G4 Filename UG4T3S01.WP Cell 1-5 vial 1 min-5 min Filename UG4T3S16.WP Cell 1-5 vial 6 min-10 min Filename UG4T3S31.WP Cell 1-5 vial 11 min-15 min Filename UG4T3S46.WP Cell 1-5 vial 16 min-20 min Gas=Xenon G5 Filename UG5T3S01.WP Cell 1-5 vial 1 min-5 min Filename UG5T3S16.WP Cell 1-5 vial 6 min-10 min Filename UG5T3S31.WP Cell 1-5 vial 11 min-15 min Filename UG5T3S46.WP Cell 1-5 vial 16 min-20 min Gas=Oxygen G6 Filename UG6T3S01.WP Cell 1-5 vial 1 min-5 min Filename UG6T3S16.WP Cell 1-5 vial 6 min-10 min Filename UG6T3S31.WP Cell 1-5 vial 11 min-15 min Filename UG6T3S46.WP Cell 1-5 vial 16 min-20 min Gas=Neon Filename UG7T3S01.WP Cell 1-5 vial 1 min-5 min Filename UG7T3S16.WP Cell 1-5 vial 6 min-10 min Filename UG7T3S31.WP Cell 1-5 vial 11 min-15 min Filename UG7T3S46.WP Cell 1-5 vial 16 min-20 min RESULTS HAVE BEEN ENTERED IN A LOTUS MATRIX: UREAT3.WK3 (Disk Urease'92).

EXAMPLE 5

Glucose Oxidase/Glucose/$H_2O_2$/Perixidase Kit 315-100 Gas Run Protocol

SIGMA Diagnostic Kit 315-100 (Procedure No. 315)

| ENZYME: | Glucose oxidase [*Aspergillus niger*]: 15,000 U/L<br>Peroxidase (Horseradish): 10,000 U/L<br>Contained in the Glucose [Trinder] Reagent 315-100<br>Lot# 68F-6158 |
|---|---|
| SUBSTRATE: | 0.25 mg/ml Glucose solution in pH 7.2 TRIS buffer<br>[Dextrose USP, Fisher, Lot# 870657] |
| DILUTENT: | TRIS buffer pH 7.2 at 25° C. |
| PRINCIPLE: | |

$$\text{Glucose} + 2H_2O + O_2 \xrightarrow{\text{Glucose oxidase}} \text{Gluconic acid} + H_2O$$

$$2H_2O_2 + \text{4-aminoantipyrine} + \text{p-Hydroxybenzene sulfonate} \xrightarrow{\text{Peroxidase}} \text{Quinoeimine Dye} + 4H_2O$$

KIT CALIBRATION PROCEDURE:
SIGMA PROCEDURE
Total volume in cuvette: 1.005 ml
1 ml Glucose [Trinder] Reagent
5 μL Glucose solution with a linearity top limit of 750 mg/dl
Enzyme/Substrate content per cuvette:
Glucose oxidase: 15 Units
Peroxidase: 10 Units
Glucose (Linearity top limit): 37.5 μg
Enzyme/Substrate concentrations in cuvette ($V_{tot}$=1.005 ml):
Glucose oxidase: 15 U/ml
Peroxidase: 10 U/ml
Glucose (Linearity top limit): 37.3 μg/ml
TESTING PROCEDURE

| Enzyme/Substrate content per cuvette: | |
|---|---|
| Glucose oxidase: | 15 Units |
| Peroxidase: | 10 Units |
| Glucose: | |
| S1 | 25 μg |
| S2 | 50 μg |
| S3 | 75 μg |
| S4 | 100 μg |
| S5 | 125 μg |
| Enzyme/Substrate concentrations in cuvette ($V_{tot}$ = 2.5 ml): | |
| Glucose oxidase: | 6 U/ml |
| Peroxidase: | 4 U/ml |
| Glucose: | |
| S1 | 10 μg/ml |
| S2 | 20 μg/ml |
| S3 | 30 μg/ml |
| S4 | 40 μg/ml |
| S5 | 50 μg/ml |

PARAMETERS

| Gaseous atmospheres: |
|---|
| G1 Air |
| G2 Neon |
| G3 Argon |
| G4 Krypton |
| G5 Xenon |
| G6 Oxygen |
| G7 Nitrogen |
| Temperatures: |
| T1 10° C. |
| T2 25° C. |

5 substrate concentrations:

| | Glucose [Trinder] Reagent [ml] | Tris Buffer pH 7.2 [ml] | Glucose Solution [0.25 mg/ml] [ml] |
|---|---|---|---|
| S1 | 1.0 | 1.4 | 0.1 |
| S2 | 1.0 | 1.3 | 0.2 |
| S3 | 1.0 | 1.2 | 0.3 |
| S4 | 1.0 | 1.1 | 0.4 |
| S5 | 1.0 | 1.0 | 0.5 |

Blank:
R 1 ml Glucose [Trinder] Reagent+1.5 ml TRIS

A solution with a ratio 1:1.5 Glucose [Trinder] Reagent:Tris buffer was prepared. Two cuvettes were filled with 2.5 ml each of this solution. These are the reference cuvettes. The blank was changed for each temperature.

SOLUTION PREPARATION

| Soln A: | TRIS buffer pH 7.2 at 25° C.<br>Dissolve 7.02 g Trizma HCl (T-3253) and 0.67 g Trizma Base (T-1503) in 1 liter of $H_2O$. Adjust pH. |
|---|---|
| Soln B: | Glucose [Trinder] reagent<br>Reconstitute according to the directions (Procedure No. 315) with 100 ml D.I. $H_2O$ |
| | 4-Aminoantipyrine 0.5 mmol/L |
| | p-Hydroxybenzene Sulfonate 20 mmol/L |
| | Glucose Oxidase [*Aspergillus niger*] 15,000 U/L |
| | Peroxidase [Horseradish] 10,000 U/L |
| | Buffer pH 7.0 ± .1 |
| | Stabilizers and Fillers |
| | Stored in refrigerator (0–5° C.) in a Nalgene bottle (wrapped in aluminium foil and put in a carton box to protect from strong light). |
| Soln C: | 0.25 mg/ml Glucose solution in TRIS buffer<br>Dissolve 25 mg in 100 ml Soln A. |

TDrive, 25° C., 505 nm, 80 pts, 15 s int. (20 min)

S = 2.0 ml Soln B + 0.5 ml Soln C
R = 2.0 ml Soln B + 0.5 ml Soln A

315CHK01.SP

Material Needed:
Siliconed acrylic covets:

$$\frac{7 \times 5 \times 2(G \times S)}{72 \text{ cuvettes}} \frac{2}{\text{(B9)}}$$

TRIS buffer pH 7.2 (25° C.): 186 ml
Glucose [Trinder] Reagent solution: 72 ml
Glucose solution (0.25 mg/ml): 42 ml
Serum vials (10 cc): 7 (6 ml/each)
Needles: B-D 22G½
PROCEDURE
Label silicone-sealed cuvettes (B9T?G?S?)
Purge cuvettes with air (3×10 cc)
Fill the cuvettes with the required amount of TRIS buffer (see previous table) with a 1 cc syringe.
Add 1 ml of Glucose [Trinder] Reagent to cuvettes with a 1 cc syringe.
Keep cuvettes in refrigerator in the dark.
Fill serum vials with Glucose solution (0.25 mg/ml).
Keep serum vials in refrigerator.
Inject 3×10 cc of the appropriate gas in silicone-sealed cuvettes and serum vials.
Store cuvettes and serum vials overnight in refrigerator
(0°–5° C.) under two 10 cc syringes. Cuvette are kept in the dark (carton box) to protect from strong light.
RUNS: Jan. 23, 1990
PARAMETERS:
Slit 1 nm
speed 1,500 nm/min
Asave Y
Aprint N

| CPRG | 5 cells |
|---|---|
|  | 505 nm |
|  | $Y_{max} = 1.3$ |
| 1. ([S1, S2, S3, S4, S5], G1, T1, B9) | 20 min |
| 52. ([S1, S2, S3, S4, S5], G5, T1, B9) | 20 min |
| 3. ([S1, S2, S3, S4, S5], G7, T1, B9) | 20 min |
| 4. ([S1, S2, S3, S4, S5], G4, T1, B9) | 20 min |
| 5. ([S1, S2, S3, S4, S5], G3, T1, B9) | 20 min |
| 6. ([S1, S2, S3, S4, S5], G2, T1, B9) | 20 min |
| 107. ([S1, S2, S3, S4, S5], G6, T1, B9) | 20 min |
|  | 2 HR 20 min |
| 1. ([S1, S2, S3, S4, S5], G1, T1, B9) | 20 min |
| 2. ([S1, S2, S3, S4, S5], G5, T1, B9) | 20 min |
| 153. ([S1, S2, S3, S4, S5], G7, T1, B9) | 20 min |
| 4. ([S1, S2, S3, S4, S5], G4, T1, B9) | 20 min |
| 5. ([S1, S2, S3, S4, S5], G3, T1, B9) | 20 min |
| 6. ([S1, S2, S3, S4, S5], G2, T1, B9) | 20 min |
| 7. ([S1, S2, S3, S4, S5], G6, T1, B9) | 20 min |
|  | 2 HR 20 min |

SCHEDULE

| spectrophotometer set-up | | |
|---|---|---|
| PARAM: | ABS | |
|  | slit 1 nm | |
|  | speed 1,500 nm/min | |
|  | Asave Y | |
|  | Aprnt N | |
| Background correction: | 900–190 nm | |
| CPRG | 5 cells | |
|  | 505 nm | |
|  | Pts 80 | ===>20 min RUN int 15 |
|  | $Y_{min} = 0$—0 | |
|  | $Y_{max} = 1.3$ | |

Set Digital controller on 10° C. and Fisher circulator on 5° C. and high pump speed). Hook $N_2$ to spectrophotometer and have a continuous flow of 20 psi throughout the experiment to prevent condensation on the outside of the cuvettes.

Remove the T1G1 cuvettes out from the refrigerator. Bubble 3×10 cc of G1. Return cuvette to refrigerator.

Remove G1 vial from the refrigerator. Bubble 3×10 cc of G1. Return vials to refrigerator.

Remove T1G1 cuvettes from refrigerator. Remove syringes from cuvettes. Tap cuvettes to eliminate bubbles. Put cuvettes in cell holder.

Remove G1 vial from refrigerator. Sample Glucose solution (0.25 mg/ml) with 1 cc syringes previously filled with the appropriate gas, push syringes thru silicone plugs but not into the solution. Simultaneously push syringes fully into the cuvettes then simultaneously push plungers. Start CPRG.

Continue the above procedure for the rest of the gases at both temperatures.

For 25° C., set Digital controller to 25° C. and the Fisher circulator to 20° C., and high pump speed.

| SPECTRA FILES: |
|---|
| B9T1G1S1 ... 5.SP |
| B9T1G5S1 ... 5.SP |
| B9T1G7S1 ... 5.SP |
| B9T1G4S1 ... 5.SP |
| B9T1G3S1 ... 5.SP |
| B9T1G2S1 ... 5.SP |
| B9T1G6S1 ... 5.SP |
| 35 FILES |
| B9T2G1S1 ... 5.SP |
| B9T2G5S1 ... 5.SP |
| B9T2G7S1 ... 5.SP |
| B9T2G4S1 ... 5.SP |
| B9T2G3S1 ... S.SP |
| B9T2G2S1 ... 5.SP |
| B9T2G6S1 ... 5.SP |
| 35 FILES |

EXAMPLE 6

Alcohol [Ethanol] Diagnostic Kit Sigma Diagnostic Kit No. 332-UV Gas Run Protocol SIGMA Diagnostic Kit 332-BT (Procedure No. 332-UV)
ENZYME
NAD-ADH SINGLE ASSAY VIALS (No. 330-1)
3-ml size
Lot# 657-F8
The NAD-ADH vials, when reconstituted according to the directions, contain approximately the following concentrations of active ingredients: NAD, 0.6 μmol/ml, alcohol dehydrogenase [yeast], 50 U/ml, and stabilizers.
SUBSTRATE
ETHANOL STANDARD SOLUTION (No. 330-20)
0.08% [w/v]
Lot# 118F-6093
DILUTENT
GLYCINE BUFFER REAGENT (No. 332-9)
Glycine, 0.5 mol/L, pH 9.0, and trapping agent
Lot# 78F-6118
PARAMETERS

| Gaseous atmospheres: | |
|---|---|
| G1 | Air |
| G2 | Neon |
| G3 | Argon |
| G4 | Krypton |
| G5 | Xenon |
| G6 | Oxygen |
| G7 | Nitrogen |
| Temperatures: | |
| T1 | 10° C. |
| T2 | 25° C. |

Substrate Preparation

Step 1: Prepare diluted Ethanol Standard Solution by mixing 4.0 ml Glycine Buffer Reagent (332-9) with 0.5 ml Ethanol Standard Solution (330-20). Cap until ready for use. 4 substrate concentrations:

| | Glycine Buffer Reagent 332-9 [ml] | Diluted Ethanol Standard from step 1 [ml] | Ethanol Content % [w/v] |
|---|---|---|---|
| S1 | 2.90 | 0.1 | 0.08 |
| S2 | 2.80 | 0.2 | 0.16 |
| S3 | 2.70 | 0.3 | 0.24 |
| S4 | 2.60 | 0.4 | 0.32 |

Blank

| Materials Needed: | |
|---|---|
| day 1 | |
| Siliconed acrylic cuvettes: | 7 × 4 (G × S) |
| | 1 (B5) |
| | 29 cuvettes |
| NAD—ADH Single Assay Vials: | 29 vials |
| Ethanol Standard Solution: | 3 × 0.5 ml |
| Glycine Buffer Reagent: | 105 ml |
| | 12 ml (Diluted Ethanol Standard) |
| | 117 ml |
| Serum vials (10 cc): 3 (4.5 ml Diluted Ethanol Standard/each) | |
| day 2 | |
| Siliconed acrylic cuvettes: | 7 × 4 (G × S) |
| | 1 (B5) |
| | 29 cuvettes |
| NAD—ADH Single Assay Vials: | 29 vials |
| Ethanol Standard Solution: | 3 × 0.5 ml |
| Glycine Buffer Reagent: | 105 ml |
| | 12 ml (Diluted Ethanol Standard) |
| 117 ml | |
| Serum vials (10 cc): 3 (4.5 ml Diluted Ethanol Standard/each) | |

Blank
R=1 NAD-ADH Assay Vial (330-1)+3.0 ml 332-9
RUNS

| 11/30/89 | | |
|---|---|---|
| 1. | ([S1, S2, S3, S4], G1, T1, B5) | 20 min |
| 2. | ([S1, S2, S3, S4], G5, T1, B5) | 20 min |
| 3. | ([S1, S2, S3, S4], G4, T1, B5) | 20 min |
| 4. | ([S1, S2, S3, S4], G3, T1, B5) | 20 min |
| 5. | ([S1, S2, S3, S4], G2, T1, B5) | 20 min |
| 6. | ([S1, S2, S3, S4], G6, T1, B5) | 20 min |
| 7. | ([S1, S2, S3, S4], G7, T1, B5) | 20 min |
| | | 2 HR 20 min |
| 12/01/89 | | |

-continued

| 1. | ([S1, S2, S3, S4], G1, T2, B5) | 10 min |
|---|---|---|
| 2. | ([S1, S2, S3, S4], G5, T2, B5) | 10 min |
| 3. | ([S1, S2, S3, S4], G4, T2, B5) | 10 min |
| 4. | ([S1, S2, S3, S4], G3, T2, B5) | 10 min |
| 5. | ([S1, S2, S3, S4], G2, T2, B5) | 10 min |
| 6. | ([S1, S2, S3, S4], G6, T2, B5) | 10 min |
| 7. | ([S1, S2, S3, S4], G7, T2, B5) | 10 min |
| | | 1 HR 10 min |

SAMPLE PREPARATION

Purge silicone-sealed cuvettes with air
Label NAD-ADH vials (S1 . . . 4, B5)
Pipet Glycine buffer with 1 ml disposable pipets.
Pour the required amount (see table) in the NAD-ADH vials:
Cap and invert gently several times to dissolve contents. DO NOT SHAKE.
Put in fridge (0°–5° C.), in the dark.
Transfer contents of tubes to appropriately numbered silicone-sealed cuvettes (B5T1G?S?) by means of a 3 cc disposable syringe+needle.
Keep cuvettes in fridge, in the dark.
Inject 1×3 cc of gas in silicone-sealed cuvettes No 2nd and 3rd 3 cc gas injection: NAD-ADH solution squirts back in the syringes because of foam formation due to bubbling. Store cuvettes overnight in refrigerator (0°–5° C.) under two 3 cc syringes, in the dark.
Prepare diluted Ethanol Standard Solution by mixing 4.0 ml Glycine Buffer Reagent (332-9) with 0.5 ml Ethanol Standard Solution (330-20) in 10 cc serum vials. Cap.
Considering the volatility of ethanol and the small amounts (0.1 to 0.4) of diluted Ethanol Standard Solution, we do not find appropriate to bubble gas through the substrate solution.
Purge silicone-sealed cuvettes with air
Label NAD-ADH vials (S1 . . . 4, B5)
Pipet Glycine buffer with 1 ml disposable pipets.
Pour the required amount (see table) in the NAD-ADH vials.
Cap and invert gently several times to dissolve contents. DO NOT SHAKE.
Put in fridge (0°–5° C.), in the dark.
Transfer contents of tubes to appropriately numbered silicone-sealed cuvettes (B5T2G?S?) by means of a 3 ml disposable syringe+needle.
Keep cuvettes in fridge, in the dark.
Inject 1st 3 cc of gas in silicone-sealed cuvettes. Keep cuvettes in refrigerator under two 3 cc syringes filled up with the appropriate gas.
2nd 3 cc gas injection in silicone-sealed cuvettes. We overcome the problem of squirting back by sucking the solution in and out of the syringes. Store cuvettes overnight in refrigerator (0°–5° C.) under two 3 cc syringes, in the dark.
Prepare diluted Ethanol Standard Solution by mixing 4.0 ml Glycine Buffer Reagent (332-9) with 0.5 ml Ethanol Standard Solution (330-20) in 10 cc serum vials. Cap.
Considering the volatility of ethanol and the small amounts (0.1 to 0.4) of diluted Ethanol Standard Solution, we do not find appropriate to bubble gas through the substrate solution.
SCHEDULE

| | |
|---|---|
| PARAM: | ABS |
| | slit 1 nm |
| | speed 1,500 nm/min |
| | Asave Y |
| | Aprnt N |
| Background correction: | 900–190 nm |
| CPRG | 4 cells |
| | 340 nm |
| | 100 pts (20 min) |
| | int 12 |
| | $Y_{min} = 0.0$ |
| | $Y_{max} = 2.0$ |

Remove the G1 cuvettes out from the fridge. Bubble 2×3 cc of gas. Place cuvettes (under two 3 cc syringes filled up with the appropriate gas) in cell holder.

Remove syringes from cuvettes. Tap cuvettes to eliminate bubbles. Put cuvettes back in cell holder.

Sample diluted Ethanol Standard Solution with 1 cc syringes, pick syringes into silicone, push plungers simultaneously, run timedrives.

AND SO ON ...

| | |
|---|---|
| PARAM: | ABS |
| | slit 1 nm |
| | speed 1,500 nm/min |
| | Asave Y |
| | Aprnt N |
| Background correction: | 900–190 nm |
| CPRG | 4 cells |
| | 340 rm |
| | 50 pts (10 min) |
| | int 12 |
| | $Y_{min} = 0.0$ |
| | $Y_{max} = 2.0$ |

Remove the G1 cuvettes out from the fridge. Bubble 2×3 cc of gas. Place cuvettes (under two 3 cc syringes filled up with the appropriate gas) in cell holder.

Remove syringes from cuvettes. Tap cuvettes to eliminate bubbles. Put cuvettes back in cell holder.

Sample diluted Ethanol Standard Solution with 1 cc syringes, pick syringes into silicone, push plungers simultaneously, run timedrives.

| SPECTRA FILES: |
|---|
| B5T1G1S1...4.SP |
| B5T1G5S1...4.SP |
| B5T1G4S1...4.SP |
| B5T1G3S1...4.SP |
| B5T1G2S1...4.SP |
| B5T1G6S1...4.SP |
| B5T1G7S1...4.SP |
| 28 FILES |
| B5T2G1S1...4.SP |
| B5T2G5S1...4.SP |
| B5T2G4SI...4.SP |
| B5T2G3S1...4.SP |
| B5T2G2S1...4.SP |
| B5T2G6S1...4.SP |
| B5T2G7S1...4.SP |
| 28 FILES |

Example Results

The following consists of example results obtained from gas runs. Negative numbers indicate an inhibition of the enzyme activity. Positive numbers indicate an enhancement of the enzyme activity

TABLE 1

Alkaline Phosphatase (EC 3.1.3.1) Diagnostic Kit: Rate Difference

| T(°C.) | Air | Kr:Xe | Ar | Kr | Xe | $N_2$ |
|---|---|---|---|---|---|---|
| 10 | 0.0 | 43.3 | 33.3 | 1.7 | 16.7 | 0 |
| 25 | 0.0 | 40.9 | 3.0 | 9.1 | 18.2 | 0 |
| 35 | 0.0 | 23.2 | 30.4 | 4.3 | 7.3 | 0 |

Note: Kr:Xe is a 90:10 mix

TABLE 2

Alkaline Phosphatase (EC 3.1.3.1) Diagnostic Kit: Yield Difference

| T(°C.) | Air | Kr:Xe | Ar | Kr | Xe | $N_2$ |
|---|---|---|---|---|---|---|
| 10 | 0.0 | 43.3 | 33.3 | 1.7 | 16.7 | 0 |
| 25 | 0.0 | 40.9 | 3.0 | 9.1 | 18.2 | 0 |
| 35 | 0.0 | 23.2 | 30.4 | 4.3 | 7.3 | 0 |

Note: Kr:Xe is a 90:10 mix

FIGS. 1–3 show the improvement of the rate of the alkaline phosphatase-catalyzed reaction at 10°, 25° and 35° C. due to the saturation with the following noble gases, argon, krypton and xenon, alone or in mixtures, as illustrated by a 9:1 krypton: xenon mixture.

TABLE 3

Acid Phosphatase (EC 3.1.3.2) Diagnostic Kit: % Rate Difference

| | | % RATE DIFFERENCE | | | |
|---|---|---|---|---|---|
| T(°C.) | Air | Xr:Xe | Ar | Kr | Xe |
| 10 | 0.0 | 15.7 | 8.4 | 18.1 | 42.2 |
| 25 | 0.0 | 8.9 | 12.2 | 13.3 | 21.1 |
| 35 | 0.0 | 0.0 | −1.4 | 1.4 | 5.6 |

Note: Kr:Xe mix is a 90:10 mix

TABLE 4

Acid Phosphatase (EC 3.1.3.2) Diagnostic Kit: Yield Difference

| | | % YIELD DIFFERENCE | | | |
|---|---|---|---|---|---|
| T(°C.) | Air | Xr:Xe | Ar | Kr | Xe |
| 10 | 0.0 | 11.3 | 9.4 | 16.0 | 39.2 |
| 25 | 0.0 | 4.6 | 9.2 | 7.3 | 14.7 |
| 35 | 0.0 | −0.84 | −0.42 | 1.3 | 4.2 |

Note: Kr:Xe mix is a 90:10 mix

FIG. 4 shows the improvement of the rate of the acid phosphatase-catalyzed reaction at 10° C. due to the saturation with the following noble gases, argon, krypton and xenon, alone or in mixtures, as illustrated by a 9:1 krypton:xenon mixture.

TABLE 5

Urea Nitrogen Diagnostic Kit: % Rate Difference (Urease EC 3.5.1.5)

| | | % RATE DIFFERENCE | | | | |
|---|---|---|---|---|---|---|
| Temp | Air | Ne | Ar | Kr | Xe | $N_2$ |
| 37° C. | 0.0 | 3.1 | 9.4 | 0.0 | 9.4 | 0.0 |

TABLE 6

Urea Nitrogen Diagnostic Kit: % Yield Difference (Urease EC 3.5.1.5)

| | | | | | | |
|---|---|---|---|---|---|---|
| Temp | Air | Ne | Ar | Kr | Xe | $N_2$ |
| 37° C. | 0.0 | 3.1 | 9.4 | 0.0 | 9.4 | 0.0 |

TABLE 7

Alcohol (Ethanol), 0.08% Ethanol: % Rate Difference
(Alcohol dehydrogenase EC 1.1.1.1)

| Temp | % RATE DIFFERENCE | | |
|---|---|---|---|
|  | Air | Ar | Kr |
| 10° C. | 0.0 | 8.8 | 2.9 |

TABLE 8

Alcohol (Ethanol), 0.24% Ethanol: % Rate Difference
(Alcohol dehydrogenase EC 1.1.1.1)

| Temp | % RATE DIFFERENCE | | | |
|---|---|---|---|---|
|  | Air | Ar | Kr | Xe |
| 10° C. | 0.0 | 9.0 | 11.9 | 7.5 |
| 25° C. | 0.0 | −9.4 | −9.4 | −10.4 |

TABLE 9

Alcohol (Ethanol) 1 0. 32% Ethanol: Rate Difference
(Alcohol dehydrogenase EC 1.1.1.1)

| Temp | % RATE DIFFERENCE | | | | |
|---|---|---|---|---|---|
|  | Air | Ne | Ar | Kr | Xe |
| 10° C. | 0.0 | 12.1 | 5.2 | 8.6 | 15.6 |

TABLE 10

Alcohol (Ethanol), 0.24% Ethanol: Yield Difference
(Alcohol dehydrogenase EC 1.1.1.1)

| Temp | % YIELD DIFFERENCE | | | |
|---|---|---|---|---|
|  | Air | Ar | Kr | Xe |
| 10° C. | 0.0 | 8.3 | 14.2 | 10.0 |
| 25° C. | 0.0 | −6.6 | −4.4 | −8.0 |

TABLE 11

Alcohol (Ethanol), 0.32% Ethanol: % Yield Difference
(Alcohol dehydrogenase EC 1.1.1.1)

| Temp | % YIELD DIFFERENCE | | | | |
|---|---|---|---|---|---|
|  | Air | Ne | Ar | Kr | Xe |
| 10° C. | 0.0 | 3.9 | 2.3 | 4.7 | 10.2 |

Thus, the present invention is advantageously used to surprisingly improve the performance of diagnostic enzyme reaction systems using the gases of the present invention.

As used herein, the term "substantially" generally means at least 75%, preferably at least about 90%, and more preferably about 95%. This refers to not only duration of storage but also the volume of the containing means.

Having described the present invention, it will be apparent to one of ordinary skill in the art that many changes and modifications may be made to the above-described embodiments without departing from the spirit and the scope of the present invention.

What is claimed as new and desired to be secured by Letters Patent of the United States is:

1. A method of increasing the enzymatic reaction rate of at least one enzyme used in a diagnostic enzyme reaction system, which comprises contacting at least one reagent of said diagnostic enzyme reaction system in a reaction medium during use of the at least one reagent in conjunction with the reaction system with an effective amount of an atmosphere selected from the group consisting of a noble gas, a mixture of noble gases and a gas mixture consisting of at least one noble gas and a carrier gas;

said noble gas being selected from the group consisting of argon, neon, krypton and xenon; and
said carrier gas being selected from the group consisting of nitrogen, oxygen, nitrous oxide, helium and carbon dioxide.

2. The method of claim 1, which further comprises storing said at least one reagent under said atmosphere prior to use thereof in conjunction with said reaction system.

3. The method of claim 1, wherein said at least one reagent is contacted with said atmosphere by injecting said atmosphere, in liquid or gaseous form, into or onto said reagent.

4. The method according to claim 1, wherein the reaction medium is contacted with said atmosphere, such that the reaction medium is saturated to more than 50% volume of its full saturation level with said atmosphere.

5. The method according to claim 4, wherein the reaction medium is saturated to more than 70% volume of its full saturation level with said atmosphere.

6. The method according to claim 5, wherein the reaction medium is saturated to more than 80% volume of its full saturation level with said atmosphere.

7. The method according to claim 4, wherein said atmosphere comprises less than 50% volume of oxygen, carbon dioxide or a mixture thereof.

8. The method according to claim 7, wherein said atmosphere contains less than 30% volume of oxygen, carbon dioxide or a mixture thereof.

9. The method according to claim 8, wherein said atmosphere contains less than 20% volume of oxygen, carbon dioxide or a mixture thereof.

10. The method according to claim 9, wherein said atmosphere contains less than 10% volume of oxygen, carbon dioxide or a mixture thereof.

11. The method according to claim 1, wherein the atmosphere comprises 90 to 99% volume argon and 1 to 10% volume Xe or Kr or a mixture thereof.

12. The method according to claim 1, wherein the atmosphere comprises about 50% volume Ne and 50% volume He.

13. The method according to claim 1, wherein the atmosphere comprises about 5 to 10% volume Xe and 90 to 95% volume Kr.

14. The method according to claim 1, wherein the atmosphere comprises less than 2% volume of argon, oxygen, nitrogen or a mixture thereof.

15. The method according to claim 1, wherein the reaction medium is at a temperature between about 0° C. and 40° C.

16. The method according to claim 15, wherein the reaction medium is at a temperature between about 10° C. and 30° C.

17. The method according to claim 1, wherein the reaction medium is under a pressure of up to about 10 atmospheres.

18. The method according to claim 1, wherein the reaction medium is under a pressure of up to about 3 atmospheres.

19. The method according to claim 18, wherein the reaction medium is under a pressure of between 1 and 2 atmospheres.

20. The method according to claim 19, wherein the reaction medium is under a pressure of about 1 atmosphere.

21. The method according to claim 1, which comprises conducting a reaction of said diagnostic reaction system in a reaction medium which is substantially saturated with said noble gas, mixture of noble gases or gas mixture containing said at least one noble gas and said carrier gas.

* * * * *